United States Patent [19]

Derbyshire

[11] 4,287,011
[45] Sep. 1, 1981

[54] CLOSURE METHOD

[75] Inventor: Rodney L. Derbyshire, North Port, N.Y.

[73] Assignee: Radiation Dynamics, Inc., Melville, N.Y.

[21] Appl. No.: 38,070

[22] Filed: May 11, 1979

[51] Int. Cl.³ .................... B32B 1/08; B29C 27/00; B29B 27/24

[52] U.S. Cl. .................................... 156/85; 156/52; 156/86; 156/203; 156/227; 174/DIG. 8; 264/230; 264/342 R; 428/124; 428/212; 428/129; 428/130; 428/174; 428/913; 128/82.1; 53/427; 53/441

[58] Field of Search ............. 428/124, 121, 129, 122, 428/130, 192, 212, 913, 174; 156/82, 85, 86, 203, 204, 52, 218, 227; 264/230, 342 R, 343, DIG. 71; 138/156, 177; 206/497; 174/DIG. 8

[56] References Cited

U.S. PATENT DOCUMENTS

| | | | |
|---|---|---|---|
| 2,887,607 | 5/1959 | Millis | 138/156 |
| 3,072,517 | 1/1963 | Gaylord | 156/86 |
| 3,296,344 | 1/1967 | Timmerman | 264/560 |
| 3,679,048 | 7/1972 | Fujio | 206/497 |
| 3,700,524 | 10/1972 | Sato | 156/218 |
| 3,899,807 | 8/1975 | Sovish et al. | 428/124 |
| 3,912,154 | 10/1975 | Godar | 428/124 |
| 4,023,589 | 5/1977 | Rejeski | 138/156 |

Primary Examiner—Paul J. Thibodeau
Attorney, Agent, or Firm—Howard L. Rose

[57] ABSTRACT

A method of making a bond structure and a bond structure are provided that produce concurrently a peel bond and a lap bond. One end of a sheet to be joined to a second end of the same or other sheet is folded back on itself and on end of the other member inserted. The two pairs of contacting surfaces thus formed are subsequently bonded to each other. The bonding may be by any means and the clamping force across the bond during bonding need be applied from one side of the sheet only. By insuring that the peel bond fails before the material, a flat lap bond may be achieved by causing only the peel bond to fail.

5 Claims, 10 Drawing Figures

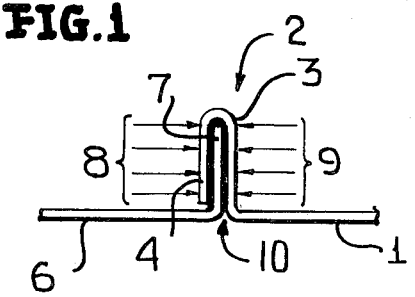
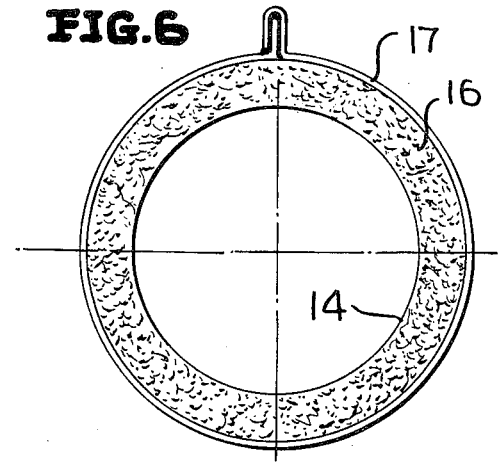
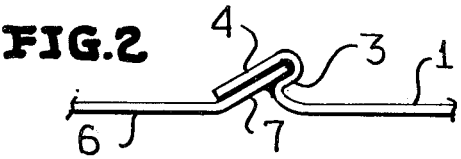
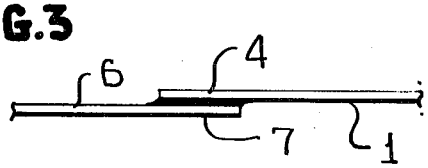
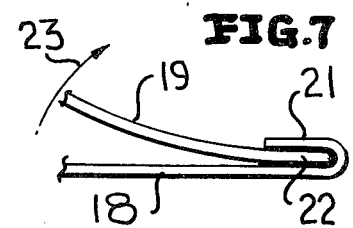
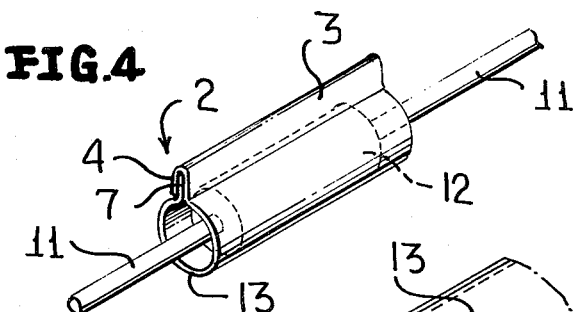
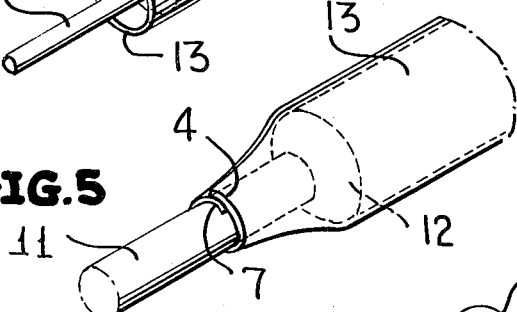
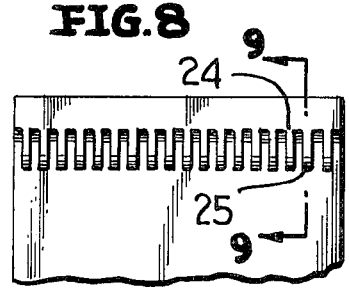
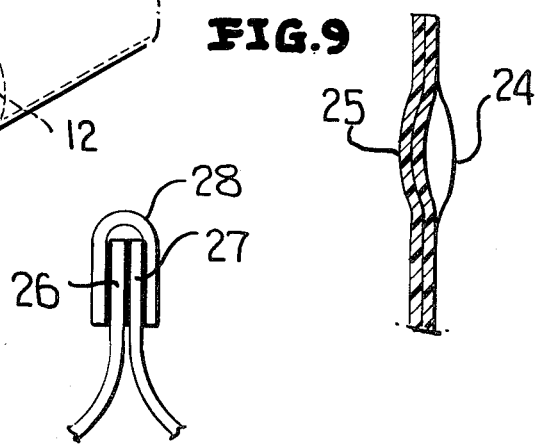

CLOSURE METHOD

FIELD OF THE INVENTION

The invention relates to a method of bonding and to a bonded structure which may constitute a permanent bonded structure or an intermediate bonded structure and more particularly to a method of bonding and a bonded structure which require access to one side only of the members to be bonded and which constitutes concurrently forming a peel bond and a lap bond arranged such that if a subsequent separating force is applied to the bonded structure it is applied initially to the peel bond.

BACKGROUND OF THE INVENTION

The term "peel bond" refers to a structure arranged such that a force tending to separate the bond tends to peel one member from the other, such as peeling the protective layer from a sticky surface.

The term "lap bond" refers to a structure arranged so that the separating force is in shear, i.e. a pull on the members in parallel but opposite directions. This latter bond is far stronger than a peel bond since in a lap bond the separating force is distributed evenly over the entire area of the bond whereas in a peel bond the separating force is at all times concentrated along the bond at the line of junction between the two bonded members.

The term "bond" as employed herein refers to any means of joining materials such as chemical bonding, heat sealing, fusion, gluing, welding, crimping, etc.

A preferred use of the present invention is to provide an easily applied waterproof sleeve about an endless cable. U.S. Pat. No. 3,899,807 to Sovish et al discusses in detail the various prior art approaches to surrounding an endless electrical cable or, more particularly, a splice or joint in such a cable, with a waterproof covering.

In such an environment it is necessary to surround a splice in an electrical cable with a waterproof sleeve. Since such a cable is, for purposes of these considerations, effectively endless it is the usual practice to wrap a loose fitting sheet of heat shrinkable material about the cable and, after applying a device for mechanically holding the edges together shrinking the material so that a tight fitting sleeve is formed about the splice. A loose fitting sleeve is normally used so that access to both of the sheets is available during application of the mechanical device or bonding of the edges if such is to be used.

Numerous different approaches have been employed to achieve the above results with access to only one side of the sheet (wrap). In U.S. Pat. Nos. 3,455,336 and 3,379,218, as examples, a heat recoverable wrap is slit, mechanically joined along specially formed edges, and subsequently shrunk and/or bonded. The resulting structures are expensive and time consuming to fabricate.

The aforesaid U.S. Pat. No. 3,899,807 provided a laminate having layers of material of different heat shrink characteristics to achieve an involute curl. Also the different materials had to be such as to be capable of being bonded to one another. In U.S. Pat. No. 3,542,077, a polymeric material is differentially irradiated so that the main body of a polymeric article is sufficiently cross-linked to be heat shrinkable while portions of the end regions are insufficiently irradiated to be heat shrinkable but are heat sealable; it being well known in the prior art that a polymeric material that is cross-linked so as to be heat shrinkable is not heat sealable and vice versa.

BRIEF SUMMARY OF THE INVENTION

According to the present invention a bonding method and structure is provided that may be formed with access to only one side of a sleeve formed of a material of uniform characteristics. The bond may be employed to apply a seamed sleeve about an object and is such that the seam may lie flat against the object or be upstanding therefrom and in either event be, if desired, water tight.

According to one embodiment of the invention, a sleeve is formed by folding one end of a sheet of material back upon itself a short distance. The opposed end of the material is disposed between the overlapped portions of the one end of the material, and each of the surfaces of the structure thus formed is bonded to its adjacent surface.

If the sleeve is to be formed about another object, the sheet is wrapped about the object and then the edges are arranged as set forth above so that the three layer lamination stands out generally perpendicular from the object. The upstanding laminate may readily be clamped from both sides and held during sealing which may be effected by any suitable means as indicated above.

The bond, at the place where the two ends of the sleeve initially come together, is a peel bond as described above and is considerably weaker than a lap bond. The strength of the peel bond is made a function of the use of the structure. If the bond is used only as a convenient method of joining two members or two ends of the same member from one side of a structure and no attempt will be subsequently made to flatten the bond, the peel bond may be made as strong as the material joined thereby. If, however, the sheet is to be shrunk or a surrounded object expanded or the sheet pulled to flatten the bond structure to a flat overlap bond only, then the peel bond should be of less strength than the material.

Various types of heat shrinkable materials are well known in the art and reference is again made to U.S. Pat. No. 3,899,807 for a discussion of various of the materials. A new polymeric material which forms the subject matter of U.S. patent application Ser. No. 038,062 filed May 11, 1979, and assigned to the same assignee as the present invention is both heat sealable and heat shrinkable and has particular application to the bonding method and structure of the present invention. A heat shrinkable polymer is generally cross-linked polymer that has been heated above its crystalline melt temperature, expanded and then cooled. The material will retain its new size but when again heated above the crystalline melt temperature, it will return to its unexpanded size.

BRIEF DESCRIPTION OF THE DRAWINGS

FIG. 1 is an end view of one form of complete bond structure of the present invention;

FIG. 2 is an end view of the bond structure of FIG. 1 with the peel bond partially peeled;

FIG. 3 is an end view of the bond structure of FIG. 1 with the peel bond completely destroyed;

FIG. 4 is a diagrammatic view of a sleeve employing the bond structure of the present invention about a cable splice;

FIG. 5 illustrates the structure of FIG. 4 after shrinking of the sleeve about the splice;

FIG. 6 is a view of a sleeve applied about a compressible material;

FIG. 7 illustrates the bond of the invention formed in the plane of the sheets to be joined;

FIG. 8 illustrates the bond of the invention formed by crimping;

FIG. 9 is a view taken along section line 9—9 of FIG. 8; and

FIG. 10 is an end view of a further embodiment of the present invention.

DETAILED DESCRIPTION OF THE INVENTION

Referring specifically to FIG. 1 of the accompanying drawings the basic bond structure is illustrated. A first member 1 illustrated as lying in the horizontal plane has an end generally designated by the reference numeral 2 formed into a generally U or V shaped member lying at right angles to the plane of member 1 and comprising vertical legs 3 and 4. A second generally horizontal member 6 has an upstanding end 7 disposed between legs 3 and 4 of member 1.

During bonding, regardless of the type of bond, compressive force or pressure may be applied across the layers (members 3, 4 and 7) in opposed directions as indicated by arrows 8 and 9 by suitable clamping or otherwise.

In use, if opposing forces are exerted on the members 1 and 6 and the peel bond is weaker than the material, the peel bond will fail at the interface of members 3 and 7 (see accompanying FIGS. 2 and 3) and the resultant structure will be the flat lap bond of FIG. 3 with the interface between members 4 and 7 in tact.

An example of a peel bond that is weaker than the material and a lap bond that is stronger is a bond structure of rubber cement with paper. The peel bond will fail before the paper and if an overlap of sufficient area is provided, the paper will fail before or concurrently with the lap bond. It is important to note that the length of the peel bond has no effect on the strength of the bond since at any time the strength of the bond attributable to size is determined only by the length of the bond at the linear junction of the joined members or the nib of the adherends; i.e. the length of the bond perpendicular to the plane of FIG. 1 at the location indicated by arrow 10. On the other hand the strength of the lap bond is a function of the area of overlap of members 1 and 6, namely, the interface between members 4 and 7. Such area may be readily varied to cause the bond to fail before the material or to be stronger than the peel bond if the former is of any significant area.

It should be noted that in the general case, however, the type of bond formed at both the lap and peel locations are identical, i.e., being formed of the same material and using the same bonding method. In these cases, the peel bond normally and rapidly fails first upon application of sufficient force, as desired, because as indicated above, in peel, stresses are concentrated at the edge of the adherends' interface and not distributed across the interface as are stresses in shear.

Referring now specifically to FIGS. 4 and 5 of the accompanying drawings, the fabrication of a waterproof sleeve about a splice in a cable is illustrated. A cable 11 has previously been spliced at some location designated by the reference numeral 12. A flat sheet of a suitable heat shrinkable polymeric material is disposed about the splice to form a wrap 13. The longitudinal edges of the wrap 13 are formed as illustrated in FIG. 4 into a preliminary bond structure defining laminates 3, 4 and 7 as illustrated in FIG. 1. The abutting surfaces of the bond structure, the interfaces between members 3 and 7 and between 4 and 7, are then secured to one another by, for instance, a suitable glue or mastic or, if appropriate and as explained subsequently, by chemical or heat sealing. Thereafter the bonded wrap is heated to cause it to shrink about the cable 11 and the splice 12, as illustrated in FIG. 5, results.

If a heat shrinkable polymeric material is to be employed, the aforesaid material of copending application Ser. No. 038062 is preferably employed. In such instance, the bond structure may be clamped between the jaws of a suitable heating mechanism and the structure heated to produce heat sealing of the adjacent surfaces. Thereafter the polymeric material is heated above its crystalline melt temperature to permit it to shrink to its normal size. With some materials, care must be taken to insure that the peel bond is of less strength than the material so that the peel bond fails. At the same time, the lap bond must be of sufficient area so that it does not fail under the shear applied by shrinking of the material.

A suitable temperature for sealing the material of the copending application is 150° C. to 250° C. for at least 3 minutes while clamped.

As previously indicated, the present invention is equally applicable to a situation in which the enclosed body or material expands. Such a situation rises where a wound is dressed or a soft cast is disposed about a broken bone and the area of the injury subsequently swells. An outer layer of material employing the bond of the invention can expand while maintaining a reasonable force to hold the dressings in place. In addition to the above application, the present invention is readily applicable to situations in which a compressible body is compressed during formation of the sleeve and subsequently expands such as in U.S. Pat. No. 4,023,589. In said patent, insulation about a thermally insulated duct is compressed during application of a wrap about the structure to provide a vapor barrier.

When the bond structure of the present invention is applied to such a structure the peel bond will fail to the extent necessary to relieve the compressive forces exerted on the insulation. Specifically, and reference is made to FIG. 6 of the accompanying drawings, a duct 14 is surrounded by a suitable thermal insulating material 16, such as fiberglass. A sleeve 17 of any material capable of providing a vapor barrier is disposed about the insulation layer 16 and bonded in accordance with the present invention by mastic or heat sealing.

Upon expansion of the layer 16 when released from a suitable sleeve forming mechanism the peel bond will fail but only to the extent required to release the internal forces in the layer 16. Thus, if the compression is such that complete failure of the peel bond is not required to release such forces, a tight fitting sleeve will still be provided.

The apparatus disclosed in said U.S. Pat. No. 4,023,589 and incorporated therein from prior patents are applicable to applying the sleeve of the present invention. The modifications required are minor and well within the knowledge of one skilled in the art.

In each of the prior examples, the seal is disclosed as being formed only from upstanding members. Referring to FIG. 7 of the accompanying drawings, there is illustrated a bond structure formed from members 18 and 19 having all regions lying in parallel planes. A flap 21 is formed along the edge of the member 18 and end region 22 is inserted under the flap. After the seal is formed the sheet 19 may be rotated as indicated by arrow 23 to break the peel bond.

As previously indicated the bond of the present invention may be formed by crimping as illustrated in FIGS. 8 and 9 of the accompanying drawings. The materials to be bonded are tightly compressed along closely spaced lines 24 and 25 to provide closely spaced, oppositely directed indentations in alternation. Such crimping may be accomplished for paper by the Paper Welder, U.S. Pat. No. De. 178,628. A peel bond made by such a process is weaker than the material.

Welding may be employed if sheet metal is utilized. Either spot welding or seam welding is suitable depending upon application of the completed structure. The techniques for controlling weld strengths are well known.

Referring now to FIG. 10 of the accompanying drawings, there is illustrated a bond utilizing the principles of the present invention in a configuration somewhat different from the other embodiments hereof.

End regions 26 and 27 of sheet like material are laid side by side and a further piece of material 28 contacts the sides of regions 26 and 27 and extends over the top thereof, all as viewed in FIG. 10.

The materials are bonded to one another at their interfaces to form a peel bond between regions 26 and 27 and lap bonds between 26 and 28 on the one hand and 27 and 28 on the other. Upon regions 26 and 27 being pulled apart, the peel bond between regions 26 and 27 fails while the lap bonds hold.

The above structure permits the use of a third length of material and does not require the end of one member to be folded over the other, a mechanical operation that with some materials may prove difficult. For instance relatively stiff materials may be bonded by means of a third and flexible length of material.

Stress has been laid on the formation of heat shrinkable sleeves about already existing bodies since such applications have existed in the past. In view of the invention of the aforesaid application Ser. No. and further in view of the present invention, the potential use of heat shrinkable preformed tubes particularly as a step in the manufacture of other products would appear to be boundless. Since in such cases the size of and configuration of the object on which the tubing is to be utilized will be known in advance, the tubes may be preformed to specific size and wall thickness.

Preformed tubing can be made on a mass production basis from endless sheets of desired width from the material of copending application Ser. No. 38,062. The folding and aligning of the longitudinally extending end regions of the sheets is readily performed by known equipment on a continuous basis as is appropriate to form the peel and lap bonds.

After formation the tube can be heated above its crystalline melting temperature, expanded and cooled at its expanded diameter to form a heat shrinkable tube of indefinite or if desired, cut length. Reference is made to U.S. Pat. No. 3,296,344.

The expansion of the tubing may follow one or the other, as desired, of two paths. The peel bond may be permitted to fail or failure may be prevented.

Failure, it is contempated, will be permitted where the crosssectional dimension of the object is known and is uniform or at least does not vary materially. In such instance control of initial sheet width and thickness is sufficient to insure a uniform covering.

Prevention of failure of the peel bond during expansion of the tubing is of particular importance in those applications where the crosssectional area of the object to be enclosed is non-uniform. Under these circumstances relatively greater and lesser failures of the peel bond may be made to accomodate size variations while permitting maintenance of relatively uniform thickness of the walls of the shrunken sleeve. If such variations could not otherwise be accomodated wall thickness variations would be the only variable available to make such accomodation; an undesirable if not fatal defect in the final product.

A novel feature of this invention is that its practice is not dependent on any particular class of materials. While some materials may be preferred, it has been shown that this method of joining is equally applicable to such dissimilar materials as plastic sheet and sheet metal.

While I have described and illustrated several specific embodiments of my invention, it will be clear that variations of the details of construction which are specifically illustrated and described may be resorted to without departing from the true spirit and scope of the invention as defined in the appended claims.

What is claimed is:

1. The method of forming an enclosure comprising
    forming an enclosure about an object from a material that has size memory and which, prior to forming the enclosure, has been heated above its crystalline melt point, expanded and cooled so that the material remains expanded until reheated,
    closing at least one side of the enclosure with the enclosure being at least as large as the object prior to reheating of the material and being smaller than the object after contraction,
    the closure being formed as a double bond between end regions of the material with one end region having a main region and a flap extending from the main region,
    disposing the other of the end regions between the flap and the main region of the one end region,
    forming bonds between adjacent surfaces of said end regions one to the other of lesser strength of peel than the strength of the material of the end regions, and
    reheating the material of the enclosure above its crystalline melt point whereby the enclosure shrinks to a size smaller than such object to produce at least partial failure of the peel bond.

2. The method of claim 1 further including the steps of:
    initially forming the bonds from a continuous length of appropriate material so as to generate a tube,
    heating said tube above its crystalline melting point,
    expanding said tube to a larger diameter and clamping the bond area to prevent failure of the peel bond,
    cooling the tube at its larger diameter.

3. The method of claim 1 wherein the bonding step comprises forming closely spaced indentation in the material in opposite directions in alternation.

4. A method of tightly enclosing an object in a material that has size memory and which prior to being placed about the object, has been heated, expanded and cooled so that it remains expanded until reheated, comprising the steps of
    forming an enclosure having at least one dimension which is at least about as large as the object when the material is expanded and is smaller than the object when the material is contracted, forming the enclosure by providing a double bond between end regions of pieces of the material or end regions of a single piece of the material the double bond having a peel bond of lesser strength than the material and a lap bond, and heating the material above its crystalline melt temperature to permit the material to revert to its contracted state causing at least partial failure of the peel bond as the enclosure shrinks to a size less than the object in at least one dimension.

5. The method of forming a sleeve about a body including the steps of:

initially forming a wrap of material about a body, forming a bond structure between the two end regions of the wrap by forming one of the end regions as a generally u-shaped member having a pair of legs and arranging the other of the end regions such that it is disposed between the legs, forming bonds between adjacent surfaces of the end regions one to the other of lesser strength in peel than the strength of the material of the end regions; and causing a relative change in size of the body and the wrap such that stress is placed across the peel bond sufficient to cause at least partial failure of the peel bond.

* * * * *